(12) United States Patent
Valletta

(10) Patent No.: US 6,248,368 B1
(45) Date of Patent: *Jun. 19, 2001

(54) USE OF MAGNESIUM BASED PRODUCTS FOR THE TREATMENT OR PROPHYLAXIS OF AUTOIMMUNE DISEASES

(76) Inventor: Giampiero Valletta, No. 188, Via Campidoglio, 03024 Ceprano (FR) (IT)

(*) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/737,743
(22) PCT Filed: May 24, 1995
(86) PCT No.: PCT/IT95/00089
  § 371 Date: Nov. 21, 1996
  § 102(e) Date: Nov. 21, 1996
(87) PCT Pub. No.: WO95/31991
  PCT Pub. Date: Nov. 30, 1995

(30) Foreign Application Priority Data

May 25, 1994 (IT) .............................. RM94A0328

(51) Int. Cl.⁷ .......................... A61K 33/42; A61K 33/14; A61K 33/06; A61K 33/12; A61K 33/08; A61K 31/19; A61K 31/195
(52) U.S. Cl. .......................... 424/601; 424/681; 424/682; 424/683; 424/692; 424/697; 514/557; 514/561
(58) Field of Search .................................... 424/601, 681, 424/682, 683, 692, 697; 514/557, 561

(56) References Cited

FOREIGN PATENT DOCUMENTS

64000016 * 1/1989 (JP).

OTHER PUBLICATIONS

Seelig et al., Trace Subst. Environ. Health, 11, 243–51 Abstract Only, 1977.*
*Concours Medical*, vol. 95, No. 43, 1973, pp. 6295–6300, J. Durlach,et al. "Magnésium et cancer."
*Facial Plastic Surgery*, vol. 7, No. 2, 1990, pp. 114–118, O. Staindl, "Hemangiomas of the Lips: Treatment with Magnesium Seeds.".
*Chemical Abstracts*, vol. 89, No. 7, Aug. 14, 1978, Columbus, Ohio, U.S.; abstract No. 53565g & JPA52044637 (Mitsubishi Chemical Industries Co.) Apr. 21, 1978.
*Chemical Abstracts*, vol. 111, No. 22, Nov. 27, 1989, Columbus, Ohio, U.S.; abstract No. 201628 & JPA06400016 (Santen Pharmaceutical Co.), Jan. 5, 1989.

* cited by examiner

Primary Examiner—Jerome D. Goldberg
(74) Attorney, Agent, or Firm—Smith, Gambrell & Russell

(57) ABSTRACT

Pharmaceutically acceptable compositions suitable for releasing magnesium ions to an organism, such as organic or inorganic magnesium salts or complexes thereof, are used to prevent and to treat neoplastic and autoimmune diseases, whose origin can be attributed to magnesium depletion. For the new therapeutic indications the magnesium based product, preferably magnesium pyrophosphate, is usually administered orally or parenterally, preferably in association with vitamin $B_6$.

25 Claims, No Drawings

USE OF MAGNESIUM BASED PRODUCTS FOR THE TREATMENT OR PROPHYLAXIS OF AUTOIMMUNE DISEASES

This application is a 371 of PCT/IT/95/00089 filed May 24, 1995.

SPECIFICATION

This invention relates to the use of magnesium containing products for the therapy and the prophylaxis of neoplastic and autoimmune diseases. More specifically, this invention relates to the use of magnesium, in the form of magnesium salts or complexes, or in any other form suitable for releasing $Mg^{++}$ ions, for the production of drugs to be administered against neoplastic or autoimmune diseases, both for prophylaxis and for therapy purposes.

It is known that magnesium is a natural element widely diffused in living organisms, specially in mammals, wherein the largest concentration thereof occurs in bones. In humans, about 60% of the total amount of magnesium is stored in the bone tissues, about 34% in the soft tissues and about 5% in the intercellular spaces. It is also well known that magnesium, being a normal component of the blood plasma and a calcium antagonist, takes part in the muscle contraction mechanism and is vital for the action of a number of enzymes.

The daily magnesium requirement for humans ranges from 5 to 10 mg/per kg of body weight, and is normally supplied through the food, particularly vegetables. A magnesium deficiency in a living organism could be associated to abnormal muscle excitability as well as convulsions. This can occur in babies from birth, when the mother was already depleted of her own magnesium reserves, or when the baby is poorly supplied with magnesium, and/or undergoes high magnesium losses from his or her organism. When encountered in an adolescent, adult or aged person, a magnesium deficiency can be ascribed to generally stressing conditions, chronic intoxication or disease, to misabsorption, to alcohol or drugs abuse, as well as to hormone pathologies that cause magnesium losses for long time periods. More specifically, a magnesium deficiency referable to a poor supply can be due, e.g., to growth, pregnancy, breast feeding, anorexia, vomiting, overload of calcium, of vitamin D, of phosphorus, of alkalizing products, or to excessive intake of alimentary fibre, to low calorie diets, to alcoholism, etc. A magnesium deficiency referable to defects in magnesium metabolism can be due, e.g., to stress or neurosis, to nervous disorders or to endocrine-metabolic disorders (J. Durlach, "Il magnesio nella pratica clinica", p. 118 and foll., IPSA, Palermo (1988)).

A magnesium deficiency or excess in an organism cannot be quantified as an absolute value, as the magnesium level in the blood is not related with the presence thereof in the deposit sites mentioned above. Generally speaking, the means for detecting the magnesium body contents include the detection of blood levels of magnesium, in the patient's plasma or in the serum (whose anomalies generally indicate a disorder in magnesium metabolism and are, normally, the starting point for a set of further specific tests); the detection of magnesium levels in the urine (which gives a measure of the elimination of magnesium via urine, and is normally associated with protein intake, being the Mg/urea ratio in the urine quite constant); the detection of magnesium levels in the spinal fluid; the detection of erythrocytic magnesium (which shows the amount of Mg contained in the bone marrow when erythropoiesis occurs and allows, therefore, an indirect medullary exploration as concerns magnesium—it is to be noted, however, that the erythrocytic magnesium level is a function of the erythrocyte age and, accordingly, a quick erythrocyte renewal is associated with an erythtocytic magnesium increase, without any reference to any magnesium excess); the detection of lymphocytic magnesium; nuclear magnetic resonance with $^{25}Mg$ (which evidences any modifications in the subcellular distribution of magnesium and in the different chemical-physical structures); and, finally, the detection of magnesium contents in the patient's bones and muscles.

According to the current medical opinion, the administration of magnesium would promote the growth of established solid tumours and generally the worsening of autoimmune diseases (see, e.g., J. Durlach, p. 215–216, cited above). Such opinion is based on the finding that erythrocytic magnesium increases when a tumour is under development or when a chronic disease, such as for example hepatic cirrhosis, shows a malignant degeneration, or when an autoimmune disease shows a recrudescence. Furthermore, the erythrocytic magnesium level would decrease when these diseases are under remission.

Specifically, at the onset of a tumoral or of an autoimmune disease a magnesium depletion takes place throughout the organism, together with a simultaneous transfer of said element from the bone marrow to the newly formed erythrocytes, and with a massive transfer of said element, carried out by the erythrocytes, to the tumoral areas or to the areas affected by the autoimmune disease. In all cases, a magnesium increase in the blood is detected. In view of that, according to the current medical opinion magnesium is the "fuel" used by the tumour or autoimmune disease to progress.

Accordingly, the conventional therapies use immunosuppressants to treat autoimmune diseases and antineoplastic chemotherapy agents to treat tumoral diseases, i.e. they use drugs aimed at reducing the cell mitotic activity in so far as it is more accelerated. These drugs actually slow down the cell metabolism (thus acting more on the affected cells than on the healthy cells), but they also cause a drastic magnesium depletion throughout the organism.

The theory according to which a solid tumoral disease can be made to regress by depleting the magnesium contents in an organism was confirmed by the findings of Parson and colleagues in 1974 (F. M. Parson et al., "Regression of malignant tumours in magnesium and potassium depletion induced by diet and haemodialysis", The Lancet, 16.02.1974), who obtained a partial regression of neoplastic lesions in some "end-stage" patients by inducing a forced magnesium depletion throughout the organism. Said depletion had been obtained by combining an almost magnesium free diet with a haemodialysis procedure, through which a high amount of magnesium was removed daily from the patient.

The validity of this therapeutic approach seems not to have been confirmed after such first attempts; however, up to now the leading medical opinion considers the admistration of magnesium as a harmful measure in respect of most neoplastic diseases and of autoimmune diseases.

According to the theory underlying the present invention, on the contrary, it has now been found that, both in man and in animals, a magnesium deficiency can actually be the origin of pathologies which are ascribable both to an excess and to a deficiency of the immune response. As it is well known, in the case of an excess of immune response, the organism shows a reactivity alteration which results in its generating autoimmune antibodies (i.e., antibodies against some components of the same generating organism), thus developing autoimmune diseases. In the case of a deficiency of said response, on the other hand, tumors or diseases from viral, bacterial, parasitic or fungal agents, that the organism is unable to defeat, could arise.

According to this invention, whether an organism depleted of magnesium shows the first or the second reaction mentioned above depends upon the variability of the genome of any single individual. Said variability makes the immune system behave hypo- or hyper-reactively according to the individual diathesis. In both cases, however, the occurrence or progression of a disease, which is the result of an inadequate immune response, has as its starting cause a magnesium deficiency.

By taking specifically into account the neoplastic diseases, it is well known that a human or animal organism generates daily about twenty tumoral cells as average. Such cells are normally recognized by the immune system as a foreign substance, on the basis of the detection of their altered gene sequences, and are then removed. When this does not occur and the immune mechanism is slowed down or made ineffective because of a magnesium deficiency, the malignant cells (poorly differentiated or even not differentiated at all, but very aggressive and not mutually bound, due to the absence of an intercellular bonding substance) develop, then overwhelming the ability of the hosting organism, the survival of which depends upon maintaining a very high differentiation level of the cell patrimony.

As to the autoimmune diseases, the difference with respect to tumoral diseases consists in the fact that in this case (which occurs in alternative to the case of tumoral diseases owing to the individual genome difference, as pointed out above) the immune system shows, instead of being hypoergic, a form of hyperactivity not intended at defending the organism, but directed against some components of the same, recognized as foreign substances. Unavoidably, this mechanism leads to a form of self-cannibalism.

In all cases, a possible latency of a disease induced by a magnesium deficiency depends mainly from the quality of the constitutional or acquired homeostatic mechanisms, of a general nature or specific for the magnesium regulation. Said quality vary from one individual to another, and it is obvious that the individual tolerance of a chronic magnesium depletion is different from one case to another, according to the quality of the magnesium homeostasis. Anyway, it is a general opinion that decompensation factors are required to cause the appearance of a symptomatology.

In view of the foregoing, according to this invention there is proposed to use magnesium, or preferably any physiologically acceptable source of $Mg^{++}$ ion, to treat solid tumoral diseases, as well as to prevent and treat autoimmune diseases.

Magnesium-containing products in the form of organic or inorganic salts, or in the form of magnesium ion complexes, are already used in therapy, mainly as antacids, laxative and purgative preparations, but also as metabolism regulators, anticonvulsants and sedatives. Obviously, it should be noted that not in all of the active substances containing magnesium ions the latter perform a true therapeutic function. In the case of magnesium sulfate, for instance, it is ackowledged that the laxative action is rather due to the osmotic conditions of the solutions employed and to the typical function of the sulfate anion, than to the properties of the magnesium ion. Therefore, the new medical indications according to this invention can be put into practice by using any magnesium compound which is able to supply the organism with $Mg^{++}$ ions in absorbable form, and which does not show further therapeutic activities incompatible with the activity considered by this invention.

Thus, the present invention specifically provides the use of a pharmaceutically acceptable magnesium salt or complex in the manufacture of a medicament for the therapy of solid neoplastic diseases and for the therapy and/or the prophylaxis of autoimmune diseases.

The pathologies that, according to the invention, are considered to be new indications of the magnesium therapy are, in the field of the neoplastic diseases the solid neoplasies (i.e., organ neoplasies) and, in the field of the autoimmune diseases, any so properly called disease, as well as any diseases showing an autoimmune mechanism. The so-called autoimmune diseases comprise rheumatoid arthritis, local and systemic scleroderma, systemic lupus erythematosus, discoid lupus erythematosus and cutaneous lupus, dermatomyositis and polymyositis, Sjögren's syndrome, nodular panarteritis, autoimmune enteropathy, proliferative glomerulonephritis, active chronic hepatitis and the polyglandular deficiency autoimmune syndrome type 1 and 2. The diseases that involve anyhow an autoimmune mechanism comprise multiple sclerosis, pemphigus vulgaris and pemphigoids, psoriasis and parapsoriasis, intestine inflammatory diseases such as the ulcerative colitis and the Chron's disease, vitiligo and sarcoidosis.

The conventional therapies for the above diseases widely vary, ranging from surgery to irradiation and physiotherapic treatments, and in most cases, to chemotherapy, using a number of different active substances, among which cortisone, immunosuppressants, interferone and corticosteroids. On the contrary, according to this invention, all of the above pathologies are to be connected with a more or less severe magnesium deficiency, which results in either an unsuitably weak or in an excessively strong immune response. Thus, a proper magnesium therapy, optionally but not necessarily associated with conventional treatments, can bring the organism to restore the correct functions of the immune system and, consequently, to defeat the above pathologies.

As to the mechanism of action, it is believed that magnesium therapy, by restoring the optimal magnesium levels, leads the immune system to increase the production of the $Th_1$ sub-population of T-helper lymphocytes, thus increasing the cell-mediated immune system response. Actually, it is well known that $Th_1$ lymphocytes mainly secrete interleukin 2 and gamma interferon, and that these cytokines stimulate a cell-mediated response, that removes the infected elements from the organism (Mossmann and Coffmann, DNAX Research Institute, Palo Alto, Calif.).

The magnesium based compound to be used in the therapy according to this invention can be in the form of a stoichiometric salt or in the form of a magnesium ion complex, i.e. associated agents which enhance the absorption when orally administered. In turn, the salt can be an organic salt, such as magnesium lactate, aspartate or acetate, or an inorganic salt, such as magnesium pyrophosphate. Magnesium pyrophosphate, also known as magnesium pidolate, is the preferred compound according to this invention, and is already used as a nervous system suppressant and against hyperexcitability, muscle contractions and cramps.

The administration of magnesium based products in the therapy of neoplastic or autoimmune diseases according to this invention can be made both orally and parenterally and, in the latter case, both through intramuscular and intravenous injections. In some cases a dermal or mucosal administration is also advantageous, as is shown in the following description.

As previously indicated, the magnesium can be used both alone and associated with the medicaments conventionally used against the concerned diseases. In the latter case, the magnesium treatment could be carried out before, during or after the conventional therapy, in order to restore a normal immune response.

Taking into account that the average magnesium requirement in an adult is 6 mg per kg of body weight per day, and that such requirement strongly increases, up to double this amount, during the catabolism stages (e.g., diseases), the therapeutic dose for oral administration in such cases has to range from 2 to 12 mg of magnesium per kg of body weight daily, preferably from 8 to 10 mg per kg of body weight daily. When using magnesium pyrophosphate, this amount is equivalent to 25–148 mg/kg body weight daily, preferably 95–123 mg/kg body weight daily. However, the optimal amount is about 9 mg of $Mg^{++}$ per kg of body weight daily, i.e. 111 mg of magnesium pyrophosphate/kg body weight daily.

When oral administration is poorly tolerated, resulting, e.g., in diarrhoea, or when misabsorption, vomiting and coma occur, or the patient is under aesthesia, etc., parenteral administration is employed, with magnesium doses ranging from 2 to 30 mg/kg body weight daily, corresponding to 25–368 mg/kg body weight daily of magnesium pyrophosphate. In most cases magnesium amounts ranging from 8 to 10 mg/kg body weight daily (i.e. 98–123 mg/kg body weight daily of magnesium pyrophosphate) are sufficient.

The same amounts of orally or parenterally administered magnesium are generally effective for newborns, babies, children and youngsters. Anyhow, the dosage depends not only upon the body weight, but also upon the patient's age and tolerance and upon stage of the disease. The highest amounts will be administered in the most severe cases of the above diseases (e.g., tumors with local or replicated metastases) by continuous infusion throughout 24 hours. The daily magnesium dose is to be diluted in a phleboclysis so as to supply the organism with no more than 80–100 mg of magnesium per hour.

It should also be considered that both parenteral and oral magnesium therapy in pharmacodynamic doses are to be associated with monitoring of the patient's plasma-magnesium level, pulsation, arterial pressure, bone-tendinous reflexes, electrocardiogram and respiration rhythm.

As an alternative to the intravenous administration the intramuscular ruote can be employed, by injecting 2–4 mg of $Mg^{++}$/kg body weight daily (equivalent to 25–45 mg of magnesium pyrophosphate/kg body weight daily) divided into one or two administrations, until the oral or intravenous route can be employed.

In the frame of the magnesium therapy as suggested by this invention, care should be taken to prevent any magnesium excess, the consequences of which are as follows:
  when the blood magnesium levels are below 1.5 mmol/l any magnesium excess is masked;
  for blood magnesium levels over 1.5 mmol/l hypotension, transient tachycardia followed by bradycardia, as well as nausea, vomiting and headache are possible;
  blood magnesium levels over 2 mmol/l result in reduced tendon reflex, muscle hypotony and sleepiness, oliguresis, extension of the sections P–R and Q–T of the electrocardiogram;
  when the blood magnesium levels are over 4 mmol/l, a total loss of tendon reflex is shown, followed by myoparalysis, specially respiratory paralysis, followed by hypothermic coma and cardiac arrest.

It should be noted that a magnesium excess, if any, can be treated with intravenous administration of calcium, osmotic diuresis, administration of anticholinesterases, analeptics and glycoside cardiotonics and, in the most severe cases, with artificial respiration and dialysis.

The contraindications in respect of an oral or parenteral magnesium therapy comprise the simultaneous administration of drugs having a curarizing effect on the motor plate (gentamicin, streptomycin, amikacin, tobramycin among the antibiotics; quinidine-based drugs among the antiarrythmics; hydantoins among the antiepilectics; diazepam and phenothiazines, etc. among the sedatives); of high doses of hypnotics and barbiturates, that depress the respiration center; of corticotherapy agents and betamimetics, that promote lung oedema and myocardium ischemia. A transitory contraindication can be an infection of the urinary tract, that could cause phosphorous-ammonium-magnesium salts to precipitate; accordingly, any urinary tract infection must be treated before starting a magnesium treatment.

The magnesium therapy according to this invention can also be carried out through cutaneous or mucosal administrations, as previously indicated, by means of baths, irrigations, ointments ant the like, in order to treat the local dermal or mucosal symptoms showed in the course of the concerned diseases. The $Mg^{++}$ concentration and the administration frequency differ according to the pathology type and the affected areas.

It is convenient to associate the magnesium therapy with the administration of some magnesium fixing substances, such as vitamin $B_6$, in order to improve the magnesium transfer, to increase the plasma levels of magnesium and to reduce the magnesium removal via urine. Preferably, vitamin $B_6$ is used with this aim, in a ratio with the $Mg^{++}$ ions in the range from 2:1 to 3:1, the optimal ratio being 2.5:1.

A reduced magnesium removal via urine can also be obtained through an antistress treatment (such as an hygienic life behaviour or a soft sedative treatment), or by avoiding excessive protein ingestion, or by using potassium retaining diuretics, such as amiloride or spironolactone. However, the use of potassium retaining diuretics is limited to the cases wherein the magnesium removal via urine is too high both as an absolute value and in respect of the urea contents in the urine.

A magnesium therapy carried out according to this invention leads to recovery of the previously indicated diseases within a time interval from three to twelve months, it being understood that "recovery" means the lesions disappearance and/or a reduction to negative values of the activity indexes of the disease, associated with a stop of the disease progression when such tissue lesions are produced that no "restitutio ad integrum" can take place (such as, e.g., in cases of articular ankylosis, nerve lesions, fibrotic effects on muscles, etc.).

When the complete clinical and analytical recovery has been obtained, the magnesium therapy can be discontinued, although it is convenient to repeat it in physiologic amounts each year, from March to June and from September to December, preferably with 5–6 mg of $Mg^{++}$/kg body weight daily, equivalent to 67–71 mg of magnesium pyrophosphate/kg body weight, orally administered. Also in this case it is convenient to associate the magnesium treatment with a vitamin $B_6$ administration at a ratio vitamin $B_6/Mg^{++}$ equivalent to 2.5:1. This therapy scheme with physiologic amounts is suggested to any healthy person, who wants to prevent any occurrence of the previously mentioned diseases.

The studies carried out in connection with this invention and the related clinical experiments, examples of which will be given hereafter, allow to formulate some hypoteses on the role of magnesium in neoplastic and autoimmune diseases. Such hypothesis are summarized below.

A magnesium deficiency in an organism causes a reduced blood level of magnesium in the intercellular space, and a parallel lowering of such element in the cells, which results in a permeability increase of the cell membranes. The consequent depolarization causes a reduction of the intracellular potassium and a related increase of the intracellular calcium. Therefore, such ion changements cause a reduced blood-calcium level and an increased blood-potassium level. When the magnesium deficiency is protracted, the intracellular calcium excess could cause insoluble crystals of calcium, phosphorus and magnesium to precipitate within the cells; these salts, although being not physiologically significant, in the event of a severe and prolonged magnesium deficiency increase the intracellular phosphorous contents, as well as, paradoxally, the intracellular magnesium contents. The temporary organism response observed by Parson et al. as an effect of the heavy magnesium deficiency induced in patients with end-stage cancer, as reported above, can be ascribed to such increase of the intracellular magnesium.

Similarly, the drastic magnesium depletion in an organism, as induced by the immunosupressants, causes an intracellular magnesium increase according to the pattern outlined above, and causes the same effects.

On the contrary, according to the findings of this invention, at the onset of a neoplastic or of an autoimmune disease the even scarce magnesium reserves in an organism are deemed to be used at an accelerate rhythm and in an increased amount just to fight the disease. As time elapses, the magnesium stocks of the organism, when not adequately restored, are depleted; and magnesium is drawn from any site from where it is available, including, when the disease continues, the main reserves, i.e. the bone tissues, until these reserves exhaust.

In this connection, it should be noted that it is right in the in the bone tissues that the the erythrocytes are synthesized, and that said erythrocytes will proceed, loaded with magnesium, towards the tumor sites of the affected areas, to counteract the disease development. When no magnesium therapy is carried out, the magnesium reserves shall exhaust, thereby weakening the immune system, particularly the cell-mediated section thereof.

Considering the large new-formed vascular network around a solid malignant tumor, which is considered by the current medical opinion as a penetration factor induced by the neoplasm for its own advantage, in order to improve and accelerate its infiltration into the healthy tissue, it is believed, on the contrary, that such network is a defence system of the organism against the neoplasm, aiming at allowing the suitable immuno-competent agents to reach the pathologic areas more quickly and in a higher amount, to fight the tumor most effectively.

Some clinical cases, showing the effectiveness of the treatment according to this invention against various neoplastic and autoimmune disorders, are reported below.

A 74-year-old man complained with alvus disturbance and repeated, sometimes sanguinolent, diarrhoea (4–5 times daily), associated with rectal tenesmus. A local tumor, at 6 cm from the anal margin, at three o'clock in jackknife position, was diagnosed through rectum exhamination followed by rectoscopy. The tumor consisted of a nut-like mass, with a soft and parenchymatous consistency, that could not be displaced to the underlying planes. The biopsy result was as follows: fragments of infiltrating ulcerated adenocarcinoma.

A tomography showed that the tumor had overcome the rectum walls and had given contiguity metastases at 1 cm beyond the tunica muscularis, while no remote metastases were evidenced. Further, a rectum wall thickening was shown, with the aspect of a new-formed stenosizing process.

The patient refused any therapy for a month and then started a magnesium treatment consisting of a daily administation of 500 $cm^3$ of physiologic solution, containing 6 g of magnesium pyrophosphate (i.e., 489 mg of $Mg^{++}$ daily, that is equivalent to about 9.7 mg of $Mg^{++}$/kg body weight daily). The infusion rate was adjusted to supply the patient with 80 mg of magnesium ions per hour for about 6 hours. Furthermore, a daily amount of 1200 mg of vitamin $B_6$ was associated (vitamin $B_6:Mg^{++}=2.5:1$), in four separate administrations. Vitamin $B_6$ was used together with the magnesium therapy in order to improve the magnesium intake by the cells, as no excessive urinal loss of magnesium was detected.

After one month of intravenous treatment, the therapy was continued orally, with 6 g of magnesium pyrophosphate daily (i.e., 488 mg of $Mg^{++}$ daily, corresponding to 9.7 mg of $Mg^{++}$/kg body weight daily), associated with 1200 g of vitamin $B_6$ in divided doses.

At the end of the third month of magnesium therapy, a rectum investigation and a rectoscopy showed that the previous tumoral tissue had disappeared from the whole rectum circumference, except from a point at 3 o'clock in jackknife position, wherein a 1.5 cm diameter area was still present, showing a hard consistency, an irregular shape and signs of a developing necrosis. At the end of the fourth month of therapy, the tumor area was further reduced, and had totally disappeared when a rectoscopy was carried out at the end of the fifth month of treatment. Both rectoscopy and tomography, carried out again at the end of the fifth month, showed that the heteroplastic tissue had disappeared while a normal rectal tissue was present.

A 35-year-old woman showed symptoms of an acute migrant arthritis at the wrist, at the scapula-humerus and at the dorsum pedis articulations since one year. She complained pains at the radius-carpus, at the metacarpusphalanx and tibia-tarsus articulations since two months, as well as knee pains. The latter appeared warm and swollen. The laboratory tests showed an increase of ESR (55, being 1–15 the normal range), of the rheuma test (105, with 0–40 normal range), of the PCR (15, with 0–6 normal range) and of fibrinogen (550, with 123–170 normal range), as well as a positive Waaler-Rose's reaction (normally being negative). A normochromic anaemia was also shown, while the ANA antibody research gave a positive result. However, neither bone nor joint lesions had been detected. Accordingly, a rheumatoid arthritis was diagnosed.

The magnesium therapy, that the patient started in a disease remission interval, consisted of daily administations of 6 g of magnesium pyrophosphate (equivalent to 489 mg of $Mg^{++}$, corresponding to 8.1 mg of $Mg^{++}$/kg body weight daily), by infusion in 500 $cm^3$ of physiologic solution. The infusion rate was adjusted to supply 80 mg of $Mg^{++}$ per hour for about 6 hours. Vitamin $B_6$ was associated with magnesium in the 2.5:1 ratio, i.e. in an amount of 1200 mg daily in divided doses, in order to improve the magnesium uptake. Suitable analgesic and anti-inflammatory drugs (FANS) were prescribed to soothe the articulation pains At the end of the first month of the magnesium based therapy, the patient was complaining less pains at affected articulations, which appeared less swollen, even if a moderate articulation rigidity lasted at the morning. The laboratory tests showed more favourable figures for ESR (42), as well as other parameters.

At this point the parenteral treatment was suspended and an oral therapy started with following dosage: 6 g of magnesium pyrophosphate daily in divided doses (i.e., 488 mg of $Mg^{++}$ daily, corresponding to 8.1 mg of $Mg^{++}$/kg body weight daily), as well as 1200 g of vitamin $B_6$ orally, also in divided doses.

At the end of the fourth month of treatment, any articulation tumescence had disappeared and the patient referred neither articulation pains nor morning articulation rigidity. The diagnostic values were as follows:

| ESR | 10 | (normal range: 1–15) |
|---|---|---|
| rheuma test | 21 | (normal range: 0–40) |
| reactive C protein | 2 | (normal range: 0–6) |
| Waaler-Rose's reaction | negative | (negative normally) |
| fibrinogen | 232 | (normal range: 123–370) |
| ANA antibody research | negative | (negative normally) |

A 32-year-old patient was affected since three years by a pemphigus vulgaris, that caused soft vesicles to form on the patient's face and scalp. The vesicles broke after forming, and gave rise to circular erosions, that later were covered by scabs. Then, the said lesions appeared also on the patient's trunk and oral mucosa.

The disease was treated for a long time using corticosteroids, and after two years a severe back bone osteoporosis and a knee osteonecrosis were detected. As these symptoms were related to the corticosteroid use, the treatment was discontinued and replaced by a treatment with immuno-modulators, interferon, calcitonin. Before starting the magnesium therapy, the patient showed erythema and scab lesions at the trunk and scalp, rare vesicle lesions at the limbs, as well as muscle hypotrophy at both superior and inferior limbs.

The therapy consisted in daily administering 9 g of magnesium pyrophosphate (i.e., 733 mg of $Mg^{++}$, corresponding to 9.16 mg/kg body weight daily of magnesium ions), dissolved into 500 $cm^3$ of a physiologic solution. The infusion rate was adjusted to supply 80 mg of $Mg^{++}$ per hour for about 9 hours. In order to improve the magnesium uptake, the oral administration of 1800 g/day of vitamin $B_6$, in divided doses, was associated with the intravenous magnesium treatment.

After one month of therapy, at the end of which the patient showed less articular pains and cutaneous lesions onto non-erythematous skin, an oral therapy was started, based on daily administrations of 9 g of magnesium pyrophosphate (i.e., 732 mg of $Mg^{++}$/day, equivalent to 9.15 mg of $Mg^{++}$/kg body weight daily) in divided doses. Moreover, 1800 mg of vitamin $B_6$ were administered daily, in divided doses.

At the end of the fourth month of this treatment, the trunk and limb scab lesions had disappeared, while scarce lesions were still present on the scalp. The patient still complained with some very light articulation pains. At the end of the sixth month of treatment, the articulation pains had disappeared at all, as well as any skin lesions, while the skin had recovered a normal aspect, although some light scars had been left.

A 27-year-old woman was found to be affected by an ulcerative colitis, that was treated using the conventional therapies. Some years after the end of the treatment, pains and diarrhoea appeared again and the patient was treated at first with corticosteroids, and then with immunosuppressants.

During a temporary regression stage of the disease the patient was submitted to a magnesium treatment, before which all prescribed tests were carried out, including a colonscopy. The latter revealed a hyperaemic colon mucosa in the last 50 cm, bleeding at the touch and showing microulcerative lesions. An histological test showed the presence of cryptic abscesses and inflammatory neutrophil infiltration trough the mucosa and submucosa.

The treatment comprised the parenteral administration of 6 g of magnesium pyrophosphate (489 mg of $Mg^{++}$, i.e., 8.89 mg of $Mg^{++}$/kg body weight daily), diluted into 500 $cm^3$ of physiologic solution, and the infusion was adjusted to supply the patient with 80 mg of $Mg^{++}$ per hour for 6 hours. 1200 g of orally administered vitamin $B_6$ were added in divided doses, to improve the magnesium uptake.

At the end of a two month treatment the patient reported no abdominal pains, and the diarrhoea was limited to two daily episodes only. The relults of the colonscopy were as follows: last 50 cm of the colon mucosa neither hyperaemic nor bleeding; and absence of microulcerative lesions. An histology test still showed the presence of inflammatory neutrophil infiltration in the colon mucosa. The magnesium treatment, associated with oral administration of vitamin $B_6$, was further continued for one month with the same dosage. At the end of this further period the patient referred no more abdominal pains nor diarrhoea. The last 50 cm of the colon mucosa appeared normal at colonscopy, while an histology test confirmed that the colon mucosa and submucosa were normal and any inflammatory infiltration had disappeared.

The present invention has been disclosed with specific reference to some preferred embodiments thereof, but it is to be understood that modifications and changes may be brought to it by those who are skilled in the art without departing from its true spirit and scope.

What is claimed is:

1. A method of treating autoimmune diseases sensitive to treatment with magnesium in humans and animals, which method comprises administering to a host in need thereof a composition consisting essentially of an effective amount of a pharmaceutically acceptable magnesium salt or complex.

2. The method according to claim 1, wherein said autoimmune diseases are selected from the group consisting of properly called autoimmune diseases and diseases showing an autoimmune mechanism.

3. The method according to claim 2, wherein said properly called autoimmune diseases are selected from the group consisting of rheumatoid arthritis, local and systemic scleroderma, systemic lupus erythematosus, discoid lupus erythematosus, cutaneous lupus, dermatomyositis, polymyositis, Sjögren's syndrome, nodular panarteritis, autoimmune enteropathy, proliferative glomerulonephritis, active chronic hepatitis and polyglandular deficiency autoimmune syndrome type 1 and 2.

4. The method according to claim 3, wherein said magnesium salt or complex is a pharmaceutically acceptable inorganic magnesium salt.

5. The method according to claim 3, wherein said magnesium salt or complex is a pharmaceutically acceptable organic magnesium salt.

6. The method according to claim 3, wherein said composition is administered by at least one route selected from the group consisting of orally, parenterally, cutaneously and mucosally.

7. The method according to claim 2, wherein said diseases showing an autoimmune mechanism are selected from the group consisting of multiple sclerosis, pemphigus vulgaris and pemphigoids, psoriasis, parapsoriasis, intestine inflammatory disease, ulcerative colitis, Crohn's disease, vitiligo and sarcoidosis.

8. The method according to claim 7, wherein said magnesium salt or complex is a pharmaceutically acceptable inorganic magnesium salt.

9. The method according to claim 7, wherein said magnesium salt or complex is a pharmaceutically acceptable organic magnesium salt.

10. The method according to claim 7, wherein said composition is administered by at least one route selected from the group consisting of orally, parenterally, cutaneously and mucosally.

11. The method according to claim 2, wherein said magnesium salt or complex is a pharmaceutically acceptable inorganic magnesium salt.

12. The method according to claim 2, wherein said magnesium salt or complex is a pharmaceutically acceptable organic magnesium salt.

13. The method according to claim 2, wherein said composition is administered by at least one route selected from the group consisting of orally, parenterally, cutaneously and mucosally.

14. The method according to claim 2, wherein said properly called autoimmune diseases are selected from the group consisting of local and systemic scleroderma, systemic lupus erythematosus, discoid lupus erythematosus, cutaneous lupus, dermatomyosis, polymyositis, Sjögren's syndrome, nodular panarteritis, autoimmune enteropathy, proliferative glomerulonephritis, active chronic hepatitis and polyglandular deficiency autoimmune syndrome type 1 and 2.

15. The method according to claim 14, wherein said magnesium salt or complex is a pharmaceutically acceptable inorganic magnesium salt.

16. The method according to claim 14, wherein said magnesium salt or complex is a pharmaceutically acceptable organic magnesium salt.

17. The method according to claim 14, wherein said composition is administered by at least one route selected from the group consisting of orally, parenterally, cutaneously and mucosally.

18. The method according to claim 1, wherein said magnesium salt or complex is a pharmaceutically acceptable inorganic magnesium salt.

19. The method according to claim 18, wherein said inorganic magnesium salt is magnesium pyrophosphate.

20. The method according to claim 1, wherein said magnesium salt or complex is a pharmaceutically acceptable organic magnesium salt.

21. The method according to claim 1, wherein said composition is administered by at least one route selected from the group consisting of orally, parenterally, cutaneously, and mucosally.

22. The method according to claim 1, wherein the amount of magnesium administered is from 2 to 12 mg per kg of body weight daily.

23. The method according to claim 1, wherein the amount of magnesium administered is from 8 to 10 mg per kg of body weight daily.

24. The method according to claim 23, wherein the composition is at least one member selected from the group consisting of magnesium lactate, magnesium aspartate, magnesium acetate, and magnesium pyrophosphate.

25. A method for the prophylaxis and/or the therapy of pemphigus vulgaris and pemphigoids in humans and animals, which method comprises administering to a host in need thereof an effective amount of a pharmaceutically acceptable magnesium salt or complex.

* * * * *